US00PP11398P

United States Patent [19]

Walden

[11] Patent Number: Plant 11,398

[45] Date of Patent: Jun. 6, 2000

[54] MINIATURE ROSE PLANT NAMED 'JACTINK'

[75] Inventor: John K. Walden, Thousand Oaks, Calif.

[73] Assignee: Bear Creek Gardens, Inc., Medford, Oreg.

[21] Appl. No.: 09/123,165

[22] Filed: Jul. 27, 1998

[51] Int. Cl.[7] ..... A01H 5/00

[52] U.S. Cl. ..... Plt./117

[58] Field of Search ..... Plt./117, 116

[56] References Cited

PUBLICATIONS

UPOV–ROM, 1999/02, Plant Variety Database, GTI Jouve Retrieval Software, citation for 'Jactink'.

*Primary Examiner*—Howard J. Locker

*Attorney, Agent, or Firm*—Klarquist Sparkman Campbell Leigh & Whinston, LLP

[57] ABSTRACT

A miniature rose plant having sweet fragrance; light pink buds, opening to creamy-white flowers borne singly and in clusters of three to five; upright, vigorous habit; and easy propagation from softwood cuttings.

1 Drawing Sheet

The present invention relates to a new and distinct variety of rose plant of the miniature class which was originated by me by crossing an unnamed seedling×an unnamed seedling.

The primary objective of this breeding was to produce a new miniature rose variety with 1½ to 2¼ inch open flowers borne in clusters, flowers with fragrance, and an upright, vigorous habit suitable for production from softwood cuttings and forcing in pots in a greenhouse. The objective was substantially achieved, along with other desirable improvements, as evidenced by the following unique combination of characteristics that are outstanding in the new variety and that distinguish it from its parents, as well as from all other varieties of which I am aware:

1. Sweet fragrance;
2. Light pink buds opening to creamy-white flowers borne singly and in clusters of three to five;
3. Upright, vigorous habit; and
4. Easily propagates from softwood cuttings.
5. No thorns of prickles on main canes or laterals.

Asexual reproduction of this new variety by cuttings, as performed at Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling (unnamed seedling× unnamed seedling).

*Pollen parent.*—Unnamed seedling (unnamed seedling×unnamed seedling).

Classification:

*Botanical.*—Rosa hybrida.

*Commercial.*—Miniature rose.

FLOWER

Observations made from January 1994 to July 1998, from specimens grown in a greenhouse environment at Somis, Calif.

Blooming habit: Recurrent.

Bud:

*Size.*—About ⅝ inch long when the petals start to unfurl.

*Form.*—The bud form is short, pointed ovoid.

*Color.*—When sepals first divide, bud color is White Group 155D with a light pink blush at petal edge, near Red-Purple Group 65C. When half blown, the upper sides of the petals are White Group 155D with a hint of Red-Purple Group 65C near tip, and the lower sides of the petals are White Group 155D with a hint of Red-Purple Group 65C near tip.

*Sepals.*—Color: Yellow-Green Group 144A. Surface texture: Smooth. There are three very lightly appendaged sepals. There are two unappendaged sepals with hairy edges.

*Receptacles.*—Color: Yellow-Green Group 144A. Shape: Funnel. Size: Broad, small (about ⅛"×3/16"). Surface: Hairy.

*Peduncle.*—Length: Short (¾"). Surface: Glandular. Color: Yellow-Green Group 144A. Strength: Erect.

Bloom:

*Size.*—Small. Average open size is 1¾ inches.

*Borne.*—Singly and several together in FL at clusters of three to five blooms.

*Stems.*—Strength: Normal. Average length is about 5½ inches.

*Form.*—When first open: Cupped. Permanence: Outer petals curl back.

*Petalage.*—Number of petals under normal conditions: 65–70.

*Color.*—The upper sides of the petals are White Group 155A. The reverse sides of the petals are White Group 155A. The base of each petal is Green-White Group 157B. The major color on the upper sides is White Group 155A.

*Variegations.*—None.

*Discoloration.*—At the end of the first day: White Group 155A. At the end of the third day: White Group 155B.

*Fragrance.*—Sweet, citrus blossom.

Petals:

*Texture.*—Thin.

*Shape.*—Oval, pointed.

*Form.*—Tips slightly recurved, the edges qilling to a point.

*Arrangement.*—Imbricated; shingle-like. Petaloids in the center are few, small.

*Persistence.*—Petals drop off cleanly before drying.
*Lastingness.*—On the plant: Long (10 –12 days). As a cut flower: Not tested.

Reproductive parts:
*Anthers.*—Size: Small (about 3/32"). Quantity: Few. Color: Near Yellow-Orange Group 20A. Arrangement: Mixed with petaloids.
*Filaments.*—Color: White Group 155D.
*Pollen.*—Color: Yellow-Orange Group 17C.
*Styles.*—Color: Green-White Group 157A.
*Stigmas.*—Color: Green-White Group 157C.

Plant:
*Form.*—Bush.
*Growth.*—Vigorous, dwarf, upright, compact.
*Mature plant.*—Height: 12–14 inches. Width: 14 inches.

Foliage: Number of leaflets on normal mid- stem leaves: Five or seven.
*Size.*—About 3¼ inches long×2¼ inches wide.
*Quantity.*—Normal.
*Color.*—New foliage. Upper surface: Near Greyed-Purple Group 183B. Lower Surface: Near Greyed-Purple Group 184B, rapidly turning green. Old foliage: Upper surface: Green Group 137A. Lower surface: Near Green Group 148B.
*Shape.*—Pointed oval.
*Texture.*—Upper side: Semi-glossy, smooth.
*Edge.*—Serrated.
*Serration.*—Single.
*Petiole rachis.*—Color: Yellow-Green Group 146A.
*Petiole underside.*—With prickles.
*Stipules.*—About 7/16" long.
*Disease resistance.*—Tolerant to mildew under normal growing conditions at Somis, Calif. Not tested for rust and blackspot.

Wood:
*New wood.*—Color: Yellow-Green Group 146A. Bark: Smooth.
*Old wood.*—Color: Yellow-Green Group 146A. Bark: Smooth.

Prickles:
*Quantity.*—On main canes from base: None. On laterals from main canes: None.

Small prickles:
*Quantity.*—On main stalks: None. On laterals: None.

I claim:

1. A novel rose plant of the miniature class as herein shown and described, characterized particularly as to novelty by its sweet fragrance; light pink buds, opening to creamy-white flowers borne singly and in clusters of three to five; upright, vigorous habit; and easy propagation from softwood cuttings.

* * * * *

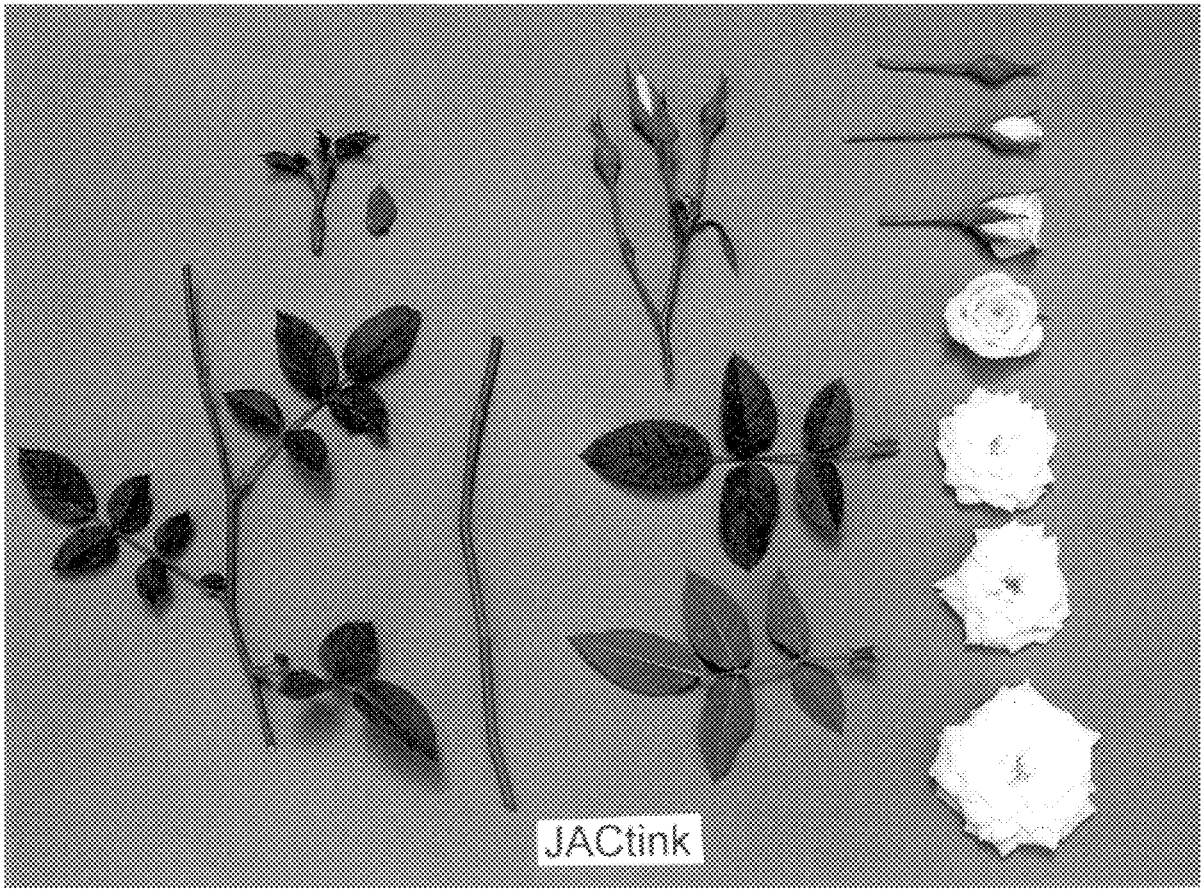
JACtink

UNITED STATES PATENT AND TRADEMARK OFFICE

CERTIFICATE OF CORRECTION

PATENT NO. : PP 11,398
DATED : June 6, 2000
INVENTOR(S) : John K. Walden

It is certified that error appears in the above-identified patent and that said Letters Patent is hereby corrected as shown below:

Column 2,
Line 23, please change "FL" to read -- flat --.
Line 44, please change "qilling" to read -- quilling --.

Column 3,
Line 21, please change "New foliage." to read -- New foliage: --.

Signed and Sealed this

Twenty-fourth Day of July, 2001

Nicholas P. Godici

*Attest:*

*Attesting Officer*

NICHOLAS P. GODICI
*Acting Director of the United States Patent and Trademark Office*